United States Patent
Coggan et al.

(10) Patent No.: US 7,563,932 B2
(45) Date of Patent: Jul. 21, 2009

(54) MICROREACTOR TECHNOLOGY TO BUCHWALD-HARTWIG AMINATION

(75) Inventors: Jennifer A. Coggan, Cambridge (CA); Emily L. Moore, Mississauga (CA); Brian J. Worfolk, Guelph (CA)

(73) Assignee: Xerox Corporation, Norwalk, CT (US)

( * ) Notice: Subject to any disclaimer, the term of this patent is extended or adjusted under 35 U.S.C. 154(b) by 150 days.

(21) Appl. No.: 11/935,028

(22) Filed: Nov. 5, 2007

(65) Prior Publication Data

US 2009/0118545 A1    May 7, 2009

(51) Int. Cl.
*C07C 209/10*    (2006.01)
(52) U.S. Cl. ..................................... 564/405
(58) Field of Classification Search ........ None
See application file for complete search history.

(56) References Cited

U.S. PATENT DOCUMENTS 6,218,576 B1    4/2001   Shintou et al.

2006/0111588 A1   5/2006  Bender et al.
2007/0100164 A1   5/2007  Coggan et al.
2008/0207851 A1*  8/2008  Schulte et al. ............. 526/64

OTHER PUBLICATIONS

Caravieilhes et al., Journal of Organometallic Chemistry (2005), 690(16), p. 3627-3629.*
U.S. Appl. No. 11/563,937, filed Nov. 28, 2006, Bender, Timothy.
U.S. Appl. No. 11/563,931, filed Nov. 28, 2006, Bender, Timothy.
U.S. Appl. No. 11/563,873, filed Nov. 28, 2006, Bender, Timothy.

* cited by examiner

*Primary Examiner*—Brian J Davis
(74) *Attorney, Agent, or Firm*—Oliff & Berridge, PLC

(57) ABSTRACT

A process for forming an arylamine compound, including reacting an arylamine and an aryl halide in the presence of a palladium ligated catalyst, a base and a suitable solvent in a microreactor.

21 Claims, No Drawings

MICROREACTOR TECHNOLOGY TO BUCHWALD-HARTWIG AMINATION

TECHNICAL FIELD

This disclosure is generally directed to an improved method for the preparation of arylamine compounds using a microreactor. In particular, this disclosure provides a method of synthesizing an arylamine using a catalyst, such as a Buchwald catalyst, under reaction conditions that include the use of a solvent, such as 1,3-dioxolane, that allows continuous reaction in a microreactor.

CROSS REFERENCE TO RELATED APPLICATIONS

Commonly assigned, U.S. patent application Publication Ser. No. 11/563,873 filed Nov. 28, 2006, describes a process for producing diarylamine compounds by the reaction of an aniline with an arylbromide compound using a ligated palladium catalyst in the presence of base.

Commonly assigned, U.S. patent application Ser. No. 11/563,931 filed Nov. 28, 2006, describes a method for producing triarylamine molecules directly by the reaction of an aniline with an arylchloride compound using a ligated palladium catalyst in the presence of base.

Commonly assigned, U.S. patent application Ser. No. 11/563,937 filed Nov. 28, 2006, describes an improved method for the preparation of derivatives of 4-aminobiphenyl using a ligated palladium catalyst in the presence of base.

Commonly assigned, U.S. patent application Ser. No. 11/263,671 filed Nov. 1, 2005, describes a process for the preparation of a tertiary arylamine compound, comprising reacting an arylhalide and an arylamine in an ionic liquid in the presence of a catalyst.

Commonly assigned, U.S. patent application Ser. No. 10/992,690 filed Nov. 22, 2004, describes a process for forming a tertiary arylamine compound, comprising reacting an arylbromide and an arylamine. For example, the application describes a process for forming N,N-diphenyl-4-aminobiphenyl, comprising reacting 4-bromobiphenyl and diphenylamine in the presence of a palladium-ligated catalyst.

The appropriate components and process aspects of each of the foregoing, such as the arylamine precursor materials and electrophotographic imaging members, may be selected for the present disclosure in embodiments thereof. The entire disclosures of the above-mentioned applications are totally incorporated herein by reference.

BACKGROUND

In image-forming apparatus such as copiers, printers, and facsimiles, electrophotographic systems in which charging, exposure, development, transfer, etc., are carried out using electrophotographic photoreceptors have been widely employed. In such image-forming apparatus, there are ever-increasing demands for speeding up of image-formation processes, improvement in image quality, miniaturization and prolonged life of the apparatus, reduction in production cost and running cost, etc.

A multi-layered photoreceptor employed in electrophotographic imaging systems sometimes includes one or more of a substrate, an undercoating layer, an intermediate layer, an optional hole- or charge-blocking layer, a charge-generating layer over an undercoating layer and/or a blocking layer, and a charge-transport layer. Additional layers such as one or more overcoat layer or layers are also sometimes included.

In the charge transport layer and the optional protective overcoat layer, hole transport molecules may be dispersed in a polymer binder. The hole transport molecules provide hole or electron transport properties, while the electrically inactive polymer binder provides mechanical properties.

Arylamine compounds can be useful as hole transport compounds in electrostatographic imaging devices and processes.

Production of arylamine hole transport compounds require the synthesis of intermediate materials, some of which generally are costly and/or time-consuming to produce, and some of which require a multi-step process.

For example, diarylamines may be produced using traditional Goldberg reactions. This method requires the derivatization of an aniline with acetic anhydride to produce an acetanilide compound. The acetanilide compound is then reacted with an arylbromide compound to produce an intermediate that must then be hydrolyzed in alcohol solution to produce the diarylamine compound. The formation of diphenylamines using the Goldberg reaction takes three reaction steps, and thus can be a lengthy process. Total cycle time for this process can be 3 to 5 days in the lab.

Diarylamines may be reacted with halogenated aryl compounds to form a variety of triarylamine compounds. See, e.g., U.S. patent application Ser. No. 10/992,690 filed Nov. 22, 2004.

Diarylamines may also be produced by subjecting an arylamine to condensation reaction in the co-presence of anhydrous aluminum chloride and anhydrous calcium chloride, as described in U.S. Pat. No. 6,218,576 B1 to Shintou et al. Both of these methods require high temperatures and harsh reaction conditions. The purity of the diarylamines obtained from these two reactions are generally low, requiring lengthy and costly purification processes.

As an alternative to the above methods, Buchwald chemistry may be important to produce arylamine compounds. The formation of di- and tri-arylamine compounds using Buchwald chemistry comprises reacting an arylamine with an aryl halide in the presence of a ligated palladium catalyst and base. This process has distinct advantages in regard to cycle time, energy consumption, and crude product purity over traditional methods.

Microreactors have been defined as "Microsystems fabricated, at least partially, by methods of microtechnology and precision engineering. Fluid channels range from 1 um (nanoreactors) to 1 mm (minireactors)." See *Microreactors*, Ehrfeld, Hessel & Lowe 2000, the entire disclosure of which is incorporated herein by reference. Typical microreactors consist of miniaturized channels, often imbedded in a flat surface referred to as the "chip." These flat surfaces can be glass plates or plates of metals such as stainless steel or Hastelloy. Microreactors have proven to be highly valuable tools in organic chemistry due to their wide flexibility of operating conditions with efficient heat transfer, optimized mixing, and high reaction control. Advantages of a microreactor over more conventional batch reactions include: faster efficient mixing, selectivity enhanced-side products and secondary reactions reduced, higher yield impurity, extreme reaction conditions, time and cost savings, and increased surface area to volume ratio that results in good mass and heat transfer. Microreactors are particularly useful for rapid optimization, screening different reaction conditions, catalysts, ligands, bases, and solvents; mechanistic studies; cost effective industrial scale up; and rapid screening for new pharmaceuticals.

Although microreactors have distinct advantages over conventional batch reaction techniques, microreactor chemistry also has its own shortcomings. For example, microreactors generally do not tolerate particulate matter well, often clogging. Since the production of arylamines through Buchwald chemistry is highly exothermic during batch production, it is ideally suited for a microreactor. However, the Buchwald synthesis of arylamines is known to produce a precipitate of solid halogen salt, such as sodium bromide, as a byproduct. Therefore, there is a need for an improved method for the preparation of arylamine compounds using a microreactor.

SUMMARY

The present disclosure addresses these and other needs, by providing an improved method for the preparation of arylamine compounds using a microreactor. More particularly, this disclosure provides a method of producing arylamine compounds, such as a di- or tri-arylamine, by reacting an arylamine with an aryl halide compound in the presence of a ligated palladium catalyst, a base and a suitable solvent in a microreactor.

In embodiments, this disclosure provides a process for forming a triarylamine compound in a mircroreactor, comprising reacting an diphenylamine with an arylbromide compound in the presence of a palladium ligated catalyst and a base while dissolved in a solvent mixture that includes toluene and at least one of 1,3-dioxolane, trihexyl(tetradecyl) phosphonium saccharin and trihexyl(tetradecyl)phosphonium bis(trifluoromethylsulfonyl)amide (IL-109).

BRIEF DESCRIPTION OF THE DRAWINGS

Not Applicable.

EMBODIMENTS

This disclosure is not limited to particular embodiments described herein, and some components and processes may be varied by one of ordinary skill in the art, based on this disclosure. The terminology used herein is for the purpose of describing particular embodiments only, and is not intended to be limiting.

In this specification and the claims that follow, singular forms such as "a," "an," and "the" include plural forms unless the content clearly dictates otherwise. In addition, reference may be made to a number of terms that shall be defined as follows:

The term "alkyl" refers, for example, to a branched or unbranched saturated hydrocarbon group, derived from an alkane and having the general formula $C_nH_{2n+1}$, wherein n is, for example, a number from 1 to about 100 or more, such as methyl, ethyl, n-propyl, isopropyl, n-butyl, isobutyl, tert-butyl, octyl, decyl, tetradecyl, hexadecyl, eicosyl, tetracosyl, and the like. The term "lower alkyl" refers, for example, to an alkyl group of from about 1 to about 12 carbon atoms. "Halogenated alkyl" refers, for example, to an alkyl group in which at least one hydrogen atom, and optionally all hydrogen atoms, is replaced by a halogen atom.

The term "aryl" refers, for example, to monocyclic or fused-ring polycyclic (i.e., rings which share adjacent pairs of carbon atoms) carbocyclic aromatic ring systems having about 6 to about 20 carbon atoms or more, such as phenyl, naphthyl, anthrycyl, and the like. Optionally, these groups may be substituted with one or more independently selected substituents, including alkyl, alkenyl, alkoxy, hydroxyl, nitro and further aryl groups. "Aryl" also includes heteroaryl groups, such as pyrimidine or thiophene.

The term "arylamine" refers, for example, to moieties containing both aryl and amine groups. Exemplary aralkylene groups have the structure Ar—NRR', in which Ar represents an aryl group and R and R' are groups that may be independently selected from hydrogen and substituted and unsubstituted alkyl, alkenyl, aryl, and other suitable functional groups. The term "triarylamine" refers, for example, to arylamine compounds having the general structure NArAr'Ar", in which Ar, Ar' and Ar" represent independently selected aryl groups.

"Amine" refers, for example, to an alkyl moiety in which one or more of the hydrogen atoms has been replaced by an —$NH_2$ group. The term "lower amine" refers, for example, to an alkyl group of about 1 to about 6 carbon atoms in which at least one, and optionally all, of the hydrogen atoms has been replaced by an —$NH_2$ group.

The terms "standard temperature" and "standard pressure" refer, for example, to the standard conditions used as a basis where properties vary with temperature and/or pressure. Standard temperature is 0° C.; standard pressure is 101,325 Pa or 760.0 mmHg. The term "room temperature" refers, for example, to temperatures in a range of from about 20° C. to about 25° C.

The terms "one or more" and "at least one" herein mean that the description includes instances in which one of the subsequently described circumstances occurs, and that the description includes instances in which more than one of the subsequently described circumstances occurs.

An improved process for producing arylamines, such as a di-arylamine or a tri-arylamine, is to react an arylhalide and an arylamine compound in the presence of a suitable catalyst and a base while dissolved in a suitable solvent in a microreactor. For example, diphenylamine can be rapidly reacted with 4-bromobiphenyl to form N,N-diphenyl-4-biphenylamine using palladium acetate ligated with tri-t-butylphosphine, and sodium t-pentoxide base, in a toluene/1,3-dioxolane solvent mixture.

According to the processes of the present invention, an arylamine and an aryl halide are used as starting materials. In embodiments, the reaction of the present disclosure, including the starting materials and final product, can generally be represented by the following reaction:

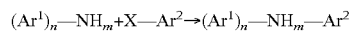

Where n is an integer value of 1 or 2; m is an integer value of 1 or 2 provided that n+m is 3; Thus, in this embodiment, an arylamine is reacted with an aryl halide to produce a di- or tri-arylamine compound.

The starting arylamine can be any suitable arylamine depending on the desired final product. $Ar^1$ independently represents any known substituted or unsubstituted aromatic component or a substituted or unsubstituted aryl group having from 2 to about 15 conjugate bonded or fused benzene rings and could include, but is not limited to, phenyl, naphthyl, anthryl, phenanthryl, and the like. The substituents on $Ar^1$ can be suitably selected to represent hydrogen, a halogen, an alkyl group having from 1 to about 20 carbon atoms, a hydrocarbon radical having from 1 to about 20 carbon atoms, an aryl group optionally substituted by one or more alkyl groups, an alkyl group containing a heteroatom such as oxygen, nitrogen, sulfur, and the like, having from 1 to about 20 carbon atoms, a hydrocarbon radical containing a heteroatom such as oxygen, nitrogen, sulfur, and the like, having from 1 to about 20 carbon atoms, an aryl group containing a heteroatom such as oxygen, nitrogen, sulfur, and the like, optionally substituted by one or more alkyl groups, and the like.

Likewise, in this reaction scheme, the aryl halide can be any suitable aryl halide depending upon the desired final product. X independently represents any suitable halide, such as fluoride, chloride, bromide, iodide, and astatide. Thus, for example, in the above reaction scheme, $Ar^2$ can be any known substituted or unsubstituted aromatic component or a substituted or unsubstituted aryl group having from 2 to about 15 conjugate bonded or fused benzene rings and could include, but is not limited to, phenyl, naphthyl, anthryl, phenanthryl, and the like. The substituents for $Ar^2$ can be groups such as, for example, hydrogen, a halogen, an alkyl group having from 1 to about 20 carbon atoms, a hydrocarbon radical having from 1 to about 20 carbon atoms, an aryl group optionally substituted by one or more alkyl groups, an alkyl group containing a heteroatom such as oxygen, nitrogen, sulfur, and the like, having from 1 to about 20 carbon atoms, a hydrocarbon radical containing a heteroatom such as oxygen, nitrogen, sulfur, and the like, having from 1 to about 20 carbon atoms, an aryl group containing a heteroatom such as oxygen, nitrogen, sulfur, and the like, optionally substituted by one or more alkyl groups, and the like.

In exemplary embodiments, $Ar^2$ can be, for example, -Phenyl-, -Phenyl-Phenyl-, -Phenyl-Phenyl-Phenyl-, or the like.

The reactants are reacted in the presence of a suitable catalyst. Although not particularly limited, suitable catalysts are those that are known or discovered to be useful for formation of nitrogen-carbon bonds. For example, suitable catalysts include ligated palladium catalysts, such as those disclosed by Buchwald et al. and Hartwig et al. (see, e.g., *J. Org. Chem.* 2000, 65, 5327-5333, the entire disclosure of which is incorporated herein by reference). In an embodiment of the present invention, an example of a suitable catalyst is palladium acetate ligated with tri-t-butylphosphine in the presence of a base.

Another specific suitable catalyst is palladium acetate ligated with 2,4,6-trioxa-1,3,5,7-tetramethyl-8-phosphaadamantane. However, it will be apparent to those skilled in the art that other ligands, such as any tertiary phosphine ligand such as biaryldialkylphosphine or trialkyl phosphine ligands, or N-heterocyclic carbene complexes could also be used to produce suitable results (from the point of view of conversion and yield), and thus would be suitable to ligate palladium or other metals and thus act as catalysts for the process described in this disclosure.

Any suitable base may be used in embodiments, such as an alkaline hydroxide or an alkaline alkoxide and the like. Exemplary bases that may be used in embodiments include bases having the general formula MOR, in which O is oxygen, M is a metal atom, and R is hydrogen or an alkyl group. M is a metal selected from potassium, sodium, lithium, calcium, magnesium and the like; and R is a hydrogen or a straight or branched alkyl group selected from methyl, ethyl, propyl, butyl, pentyl, hexyl, heptyl, octyl, nonyl, and decyl groups, such as methyl, ethyl, n-propyl, isopropyl, n-butyl, isobutyl, tert-butyl, octyl, decyl and the like. Suitable bases include potassium tert-butoxide salt, sodium tert-butoxide, and sodium tert-pentoxide.

The reaction is carried out in the presence of the catalyst, and is conducted in continuous mode.

The reaction is carried out in a suitable solvent, such as toluene, decane, other hydrocarbon solvents (either aromatic or saturated hydrocarbons), or mixtures thereof. In embodiments of the present invention, examples of suitable solvents include 1,3-dioxolane, trihexyl(tetradecyl)phosphonium saccharin (Saccarin IL) and trihexyl(tetradecyl)phosphonium bis(trifluoromethylsulfonyl)amide (IL-109). The solvent may be a mixture of the foregoing, for example about a 1:1 by volume ratio mixture of toluene:1,3-dioxolane, or about a 1:1 by volume mixture of toluene:Saccharine IL, or about a 2:1:1 by volume mixture of toluene:1,3-dioxolane:IL-109. The about 2:1:1 by volume mixture of toluene:1,3-dioxolane:IL-109 solvent in particular has been found to provide very good solubility of arylamine reactants and products, as well as by-products.

The reaction should be conducted under an atmosphere of inert gas (such as nitrogen or argon) so as to preclude deactivation of catalyst or base by oxygen or atmospheric moisture.

The reaction is conducted in a microreactor. Any suitable microreactor may be used, for example a commercial Cytos reactor manufactured by CPC Technologies. Specifically, this microreactor uses a 2 mL microreactor plate in combination with up to three 15 mL residence time plates. The residence time plates contain extended channels with good heat transfer but no active mixing elements.

The microreactor is heated by pumping heating fluid from an external bath through the heating side of the microreactor. The temperature of the microreactor can lie within wide limits, for example between 30 and 200° C., or for example between 50 and 160° C., specifically between 60 and 90° C. The streams containing the reactants and other necessary inputs can also be fed to the microreactor at different temperatures, for example a stream may be heated to approximately 40° C. Additionally, the reaction is carried out at pressures between atmospheric pressure and 100 bar, for example between atmospheric pressure and 25 bar.

The preparation of mixtures of input materials to form streams of materials may be carried out in advance in micromixers or in upstream mixing zones. The input materials are then introduced into a microreactor individually or as mixtures. For example, two streams A and B can be continuously introduced into the reactor and continuously mixed therein so that the reaction takes place. Stream A, for example, may comprise palladium acetate, tri-tert-butylphosphine and a base in a suitable solvent. Stream B, for example, may comprise an arylamine and an aryl halide in a suitable solvent.

The residence time necessary in the method according to the invention depends on various parameters, such as, for example, the temperature or reactivity of the starting materials. The term "residence time" refers to the internal volume of the reaction zone within the microreactor occupied by the reactant fluid flowing through the space divided by the average volumetric flowrate for the fluid flowing through the space, at the temperature and pressure being used. The residence time may be, for example, between about 10 minutes and about 30 minutes, or between about 20 and about 25 minutes.

It is surprising and was unforeseeable that the preparation of arylamines in a microreactor would be possible in this technically elegant manner, since it had been assumed that the production of an arylamine in a microreactor would lead to the system being clogged by halogen salt by-products.

After the reaction is completed, suitable separation, filtration, and/or purification processes can be conducted, as desired to a desired purity level. For example, the desired diarylamine product can be subjected to conventional organic washing steps, can be separated, can be decolorized (if necessary), treated with known absorbents (such as silica, alumina, and clays, if necessary) and the like. The final product can be isolated, for example, by a suitable recrystallization procedure. The final product can also be dried, for example, by air drying, vacuum drying, or the like. All of these procedures are conventional and will be apparent to those skilled in the art.

The arylamine produced by this process can be further processed and/or reacted to provide other compounds for their separate use. For example, the arylamine can be further processed and/or reacted to provide charge-transport materials or other compounds useful in such electrostatographic imaging member.

Specific examples are described in detail below. These examples are intended to be illustrative, and the materials, conditions, and process parameters set forth in these exemplary embodiments are not limiting. All parts and percentages are by weight unless otherwise indicated.

EXAMPLES

Example 1

The commercial Cytos microreactor, manufactured by CPC Technologies, is configured with three residence time units (total volume 47 mL) and heated to 70° C. Toluene is pumped through the microreactor until the reagent streams are ready to be pumped.

To a 1 L flask fitted with a mechanical stirrer, argon inlet and reflux condenser is added 9.5 g of tri-tert-butylphosphine into 1 L of anhydrous toluene to make Stock Solution A.

To a 50 mL flask fitted with mechanical stirrer, argon inlet and reflux condenser is charged palladium(II)acetate (0.072 g, 1 mol %), Stock Solution A (6.93 mL, 1 mol % tri-t-butylphosphine), and 23 mL of 1,3-dioxolane. The solution is stirred for 1 hour to allow for dissolution of palladium acetate. Then sodium t-pentoxide (3.54 g, 1 mol equivalent) is added with stirring. This solution (Solution B) was not heated.

To a second 50 mL fitted with mechanical stirrer, argon inlet and reflux condenser is charged 4-bromobiphenyl (7.5 g, 1.0 mol equivalent), diphenylamine (5.72 g, 1.05 mol equivalent) and 30 mL of 1,3-dioxolane. The solution is stirred for 10 minutes. This solution (Solution C) was not heated.

Solution B and C are each pumped at 1.0 mL/min into the microreactor via high pressure liquid chromatography (HPLC) pumps. The microreactor is maintained at 70° C. The resulting residence time in the microreactor is 23.5 minutes. The outlet stream is collected in a vial, with samples taken over 20 minutes. Conversion averaged 92% over 18 minutes.

The chemical reaction as was conducted in this example, and in the following examples, is represented as:

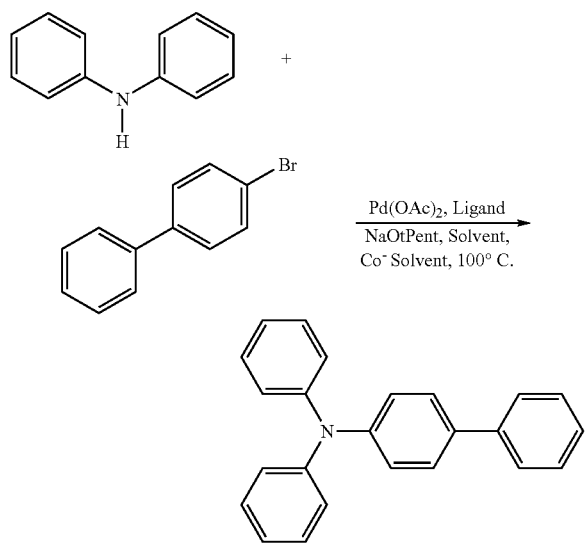

Example 2

To a 50 mL flask fitted with mechanical stirrer, argon inlet and reflux condenser is charged palladium(II)acetate (0.036 g, 1 mol %), Stock Solution A (3.47 mL, 1 mol % tri-t-butylphosphine) and 26.53 mL of anhydrous toluene. The solution is stirred for 1 hour to allow for dissolution of palladium acetate. Then sodium t-pentoxide (1.77 g, 1 mol equivalent) is added with stirring. This solution (Solution B) was not heated.

To a second 50 mL fitted with mechanical stirrer, argon inlet and reflux condenser is charged 4-bromobiphenyl (3.75 g, 1.0 mol equivalent), diphenylamine (2.86 g, 1.05 mol equivalent) and 30 mL of 1,3-dioxolane. The solution is stirred for 10 minutes. This solution (Solution C) was not heated.

Solution B and C are each pumped at 1.0 mL/min into the microreactor via HPLC pumps. The microreactor is maintained at 70° C. The resulting residence time in the microreactor is 23.5 minutes. The outlet stream is collected in a vial, with samples taken over 15 minutes. Conversion was about 51% over 20 minutes.

Example 3

The microreactor is configured with three residence time units (total volume 47 mL) and heated to 80° C. Toluene is pumped through the microreactor until the reagent solutions are ready to be pumped.

To a 50 mL flask fitted with mechanical stirrer, argon inlet and reflux condenser is charged palladium(II)acetate (0.036 g, 1 mol %), Stock Solution A (3.46 mL, 1 mol % tri-t-butylphosphine) and 27 mL of anhydrous toluene. The solution is stirred for 1 hour to allow for dissolution of palladium acetate. Then sodium t-pentoxide (1.77 g, 1 mol equivalent) is added with stirring. The solution (Solution B) is heated to 40° C. over a 30 min period.

To a second 50 mL fitted with mechanical stirrer, argon inlet and reflux condenser is charged 4-bromobiphenyl (3.75 g, 1.0 mol equivalent), diphenylamine (2.858 g, 1.05 mol equivalent) and 30 mL of 1,3-dioxolane. The solution is stirred for 10 minutes. This solution (Solution C) is heated to 40° C.

Solution B and C are each pumped at 1.0 mL/min into the microreactor via HPLC pumps. The microreactor is maintained at 80° C. The resulting residence time in the microreactor is 23.5 minutes. The outlet stream is collected in a vial, with samples taken over 20 minutes. Conversion averaged 82% over the 20 minutes.

Example 4

The same procedure as followed in Example 1, except the two Solutions B and C are each pumped at 1.5 mL/min each. The resulting residence time was 15 minutes. Again, the outlet stream was collected with samples taken over 15 minutes. Conversion was lower, averaging 50% over 15 minutes.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A process for forming a di- or tri-arylamine compound, comprising:
reacting an arylamine and an aryl halide in the presence of a palladium ligated catalyst, a base and a solvent in a microreactor.

2. The process according to claim 1, wherein the aryl halide and the arylamine are represented as follows:

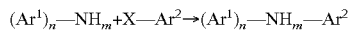

wherein:
X is a halogen;
n is an integer value of 1 or 2;
m is an integer value of 1 or 2 provided that n+m is 3;
$Ar^1$ and $Ar^2$, which can be the same or different, are selected from the group consisting of tri-, di- or mono-substituted or unsubstituted aromatic components, and substituted or unsubstituted aryl groups having from 2 to about 15 conjugate bonded or fused benzene rings, wherein a substituent on the aryl groups $Ar^1$ or $Ar^2$ is one or more of the group consisting of hydrogen, a halogen, an alkyl group having from 1 to about 20 carbon atoms, a hydrocarbon radical having from 1 to about 20 carbon atoms, an aryl group, an aryl group substituted by one or more alkyl groups, an alkyl group containing a heteroatom and having from 1 to about 20 carbon atoms, a hydrocarbon radical containing a heteroatom and having from 1 to about 20 carbon atoms, an aryl group containing a heteroatom, and an aryl group containing a heteroatom substituted by one or more alkyl groups.

3. The process according to claim 1, wherein the process is conducted in continuous mode.

4. The process according to claim 1, wherein the solvent comprises one or more of the following: toluene, 1,3-dioxolane, trihexyl(tetradecyl)phosphonium saccharin and trihexyl(tetradecyl)phosphonium bis(trifluoromethylsulfonyl)amide.

5. The process according to claim 1, wherein the solvent comprises toluene.

6. The process according to claim 1, wherein the solvent comprises 1,3-dioxolane.

7. The process according to claim 1, wherein the solvent comprises trihexyl(tetradecyl)phosphonium saccharin.

8. The process according to claim 1, wherein the solvent comprises trihexyl(tetradecyl)phosphonium bis(trifluoromethylsulfonyl)amide.

9. The process according to claim 1, wherein the solvent comprises an about 1:1 mixture by volume of toluene:1,3-dioxolane.

10. The process according to claim 1, wherein the solvent comprises an about 1:1 mixture by volume of toluene:trihexyl(tetradecyl)phosphonium saccharin.

11. The process according to claim 1, wherein the solvent comprises an about 2:1:1 mixture by volume of toluene:1,3-dioxolane:trihexyl(tetradecyl)phosphonium bis(trifluoromethylsulfonyl)amide.

12. The process according to claim 1, wherein the process is carried out under an inert atmosphere.

13. The process according to claim 1, wherein the base is represented by a general formula MOR, where:
O is oxygen;
M is a metal selected from the group consisting of potassium, sodium, lithium, calcium, magnesium; and
R is a hydrogen or a straight or branched alkyl group selected from the group consisting of methyl, ethyl, propyl, butyl, pentyl, hexyl, heptyl, octyl, nonyl, and decyl groups.

14. The process according to claim 1, wherein the base is potassium tert-butoxide salt.

15. The process according to claim 1, wherein the base is sodium t-pentoxide.

16. The process according to claim 1, wherein the base is sodium t-butoxide.

17. The process according to claim 1, wherein the catalyst is palladium acetate ligated with tri-t-butylphosphine.

18. The process according to claim 1, wherein the microreactor is heated to a temperature between 50 and 160° C.

19. The process according to claim 1, wherein the arylamine and the aryl halide are heated to a temperature of between 20 and 60° C. before being put into the microreactor.

20. The process according to claim 1, wherein a residence time in the microreactor is between about 10 minutes and about 30 minutes.

21. A process for forming a triarylamine compound comprising:
reacting an diarylamine and an aryl halide in the presence of a palladium ligated catalyst, a base and an about 1:1 mixture by volume of toluene:1,3-dioxolane in a microreactor that has been heated to a temperature between 70 and 100° C. such that a residence time in the microreactor is between about 20 and about 25 minutes.

* * * * *